(12) United States Patent
Uda et al.

(10) Patent No.: US 6,825,924 B2
(45) Date of Patent: Nov. 30, 2004

(54) DUAL PEAK WAVELENGTH TUBE, ILLUMINATOR FOR INSPECTION, INSPECTING APPARATUS, AND METHOD THEREOF

(75) Inventors: Mitsuru Uda, Shiga (JP); Tsuyoshi Iguchi, Shiga (JP); Tetsuya Nogami, Ootsu (JP)

(73) Assignee: International Business Machines Corporation, Armonk, NY (US)

( * ) Notice: Subject to any disclaimer, the term of this patent is extended or adjusted under 35 U.S.C. 154(b) by 279 days.

(21) Appl. No.: 09/734,093

(22) Filed: Dec. 11, 2000

(65) Prior Publication Data

US 2001/0015800 A1 Aug. 23, 2001

(30) Foreign Application Priority Data

Dec. 15, 1999 (JP) .......................................... 11-355455

(51) Int. Cl.$^7$ .............................................. G01N 21/00
(52) U.S. Cl. ................................ 356/237.5; 356/237.1; 356/318
(58) Field of Search ................................ 356/318, 317, 356/320, 333, 402, 414, 420, 425, 237.1–237.5; 372/34, 56, 58, 61, 65; 313/573, 594

(56) References Cited

U.S. PATENT DOCUMENTS

| | | | |
|---|---|---|---|
| 4,142,107 A | * 2/1979 | Hatzakis et al. | 250/571 |
| 4,347,001 A | * 8/1982 | Levy et al. | 356/398 |
| 4,349,277 A | * 9/1982 | Mundy et al. | 356/614 |
| 4,664,481 A | * 5/1987 | Ito et al. | 350/345 |
| 4,758,730 A | * 7/1988 | Bazin et al. | 250/571 |
| 4,952,972 A | * 8/1990 | Someya | 250/226 |
| 4,979,179 A | * 12/1990 | Segerstad et al. | 372/56 |
| 5,333,050 A | * 7/1994 | Nose et al. | 356/363 |
| 5,369,486 A | * 11/1994 | Matsumoto et al. | 356/363 |
| 5,610,477 A | * 3/1997 | Ivanov et al. | 313/573 |
| 5,610,718 A | * 3/1997 | Sentoku et al. | 356/363 |
| 5,777,744 A | * 7/1998 | Yoshii et al. | 356/394 |
| RE36,792 E | * 7/2000 | Sonehara | 348/791 |
| 6,340,824 B1 | * 1/2002 | Komoto et al. | 257/99 |

FOREIGN PATENT DOCUMENTS

| | | | |
|---|---|---|---|
| JP | 63 055 445 | * | 3/1988 |
| JP | 09 049 801 | * | 2/1997 |
| JP | 10 142 101 | * | 5/1998 |

* cited by examiner

Primary Examiner—Frank G. Font
Assistant Examiner—Sang H. Nguyen
(74) Attorney, Agent, or Firm—Thomas A. Beck; Louis Herzberg

(57) ABSTRACT

The invention provides methods and apparatus for substrate inspection and other lighting applications. It includes an lighting apparatus 10 which comprises: an illuminator 12 including a light source for emitting lights 14; supporting means for supporting an object (e.g. a patterned substrate) 18 having a finely patterned surface 16 on which predetermined patterns are formed, which is illuminated at a predetermined angle with the lights 14 from the illuminator 12; and determining means 24 for determining whether or not predetermined patterns on the surface of the object (substrate) 16 are deformed using lights 22 diffracted by the finely patterned surface 16, wherein the illuminator 12 applies two kinds of lights 14 each having a narrow wavelength range with a peak wavelength at a respective one of two complementary colors.

6 Claims, 3 Drawing Sheets

DUAL PEAK WAVELENGTH TUBE, ILLUMINATOR FOR INSPECTION, INSPECTING APPARATUS, AND METHOD THEREOF

CROSS REFERENCE

The present invention is related to a co-pending application: assigned Ser. No. 09/698423, entitled, "Defocus Visual Inspection Tool", by inventors M. Uda et al., which is incorporated herein in entirety by reference.

BACKGROUND OF THE INVENTION

1. Field of the Invention

The present invention relates to a dual peak wavelength tube, an illuminator for inspection, an inspecting apparatus and an inspecting method. More particularly, it relates to an inspecting apparatus and an inspecting method suitable for visually inspecting the presence or absence of deformations on a surface of an object, such as a wafer, caused by local defocusing by irradiating the finely patterned surface of the object/wafer formed by the photolithography method with light, and a dual peak wavelength tube used for the method.

2. Description of Related Art

In a photolithographic process for producing a semiconductor device, various factors such as line width and superposition have to be controlled. In addition, other factors such as uniformity of resist thickness also have to be controlled to prevent defocusing problems, and the like. Visual inspections for defocusing, size measurement, and overlay measurement have been conducted as in-line inspections for wafers after a resist pattern is formed by each photomask. Among these inspections, it is generally enough for size measurement and overlay measurement to make sampling tests so as to reduce the frequency of the measurement, as far as the photolithographic process is stable.

Even though a visual inspection for defocusing is a visual sensory test, this inspection is usually performed on all lots. This is because the deformation of the resist pattern, which cannot be microscopically detected in the size measurement and the overlay measurement, can be detected in a visual inspection for defocusing. Defocusing herein means a phenomenon in which the deformation of the resist pattern is caused by offset of the focus when the resist pattern is exposed to light with a stepper.

There are various causes of defocusing, such as a local protrusion on the surface caused by dirt attached to the back side of the substrate, such as a wafer, defects such as scratches on the surface of the substrate itself, and distortion of the substrate, or the difference in the film thickness of a resist coated on the surface of the substrate or displacement of the stage, or the like, which will cause deformation in the resist pattern. The defocusing may cause abnormalities such as variations in the line width of a semiconductor layer etched by the resist pattern. Accordingly, for example, in the case of gate formation of an FET (Field effect transistor), the channel length becomes shorter as the gate length becomes shorter due to defocusing, which results in nonconforming operation speed of the transistor.

If deformations of resist patterns are detected at an early stage, it is possible to reuse the substrate by stripping the resist from the substrate. On the contrary, if this visual inspection for defocusing is not very effective, late abnormality detection of the apparatus will result in unrenewable yielding loss over several lots.

There was a problem that detection of nonconformity caused by defocusing was difficult, although the visual inspection for defocusing played a very important role. More particularly, this visual inspection for defocusing is an inspecting method using a phenomenon that micron-order lines of a resist pattern (finely patterned surface) function as a diffraction grating. When lights are applied to the lines, normal parts and deformed parts in the resist pattern diffract the lights in different manners, so that the color or brightness of diffracted lights appears differently. It was very hard to discern the difference because of a slight difference of the diffracted lights in color or brightness. Thus, visual inspections have required so far considerable time and experience.

Due to these circumstances, there have been proposals for various kinds of automatic inspecting apparatuses so far. In such inspecting apparatuses, however, a conventional halogen lamp was used, which was unable to clearly discern the lights diffracted from normal portions from the lights diffracted from abnormal portions. Consequently, even if the diffracted lights are separated to take out lights within a predetermined wavelength range, and the lights are electrically detected by being converted into electrical signals using an optoelectric transducer, the detection accuracy is not good because of difficulty in detecting slight differences.

One of the inventors of the present invention previously filed the cross-referenced application, Ser. No. 09/698423, entitled, "Defocus Visual Inspection Tool", by inventors M. Uda et al. Lights illuminated by an illuminator for macro inspection according to the invention in the application comprise lights in two different colors having a sharp color contrast effect. With the use of the illuminator, lights reflected and diffracted from a portion where an abnormal resist pattern is included, and the lights reflected and diffracted from a portion where a normal resist pattern is included appear in two colors having a sharp color contrast effect. The visual inspection for reflected and diffracted lights, therefore, has made the detection of abnormal portions much easier. On the contrary, there was a fear of overlooking the abnormal portions because colors having no relation with color contrast effect might appear depending upon the direction of viewing the reflected and diffracted lights.

SUMMARY OF THE INVENTION

It is therefore an object of the present invention to provide methods and apparatus useful for inspection and other lighting applications. The methods use and the apparatus include, an illuminator, which is capable of visually detecting the presence or absence of defocusing and/or other problems on a surface of a semiconductor substrate, such as a wafer, on which resist patterns are finely formed, and widens particularly angle of visual field to improve visual inspection visibility.

BRIEF DESCRIPTION OF THE DRAWINGS

These and other objects, features, and advantages of the present invention will become apparent upon further consideration of the following detailed description of the invention when read in conjunction with the drawing figures, in which.

Reference Characters of the Drawings

Figure 1:
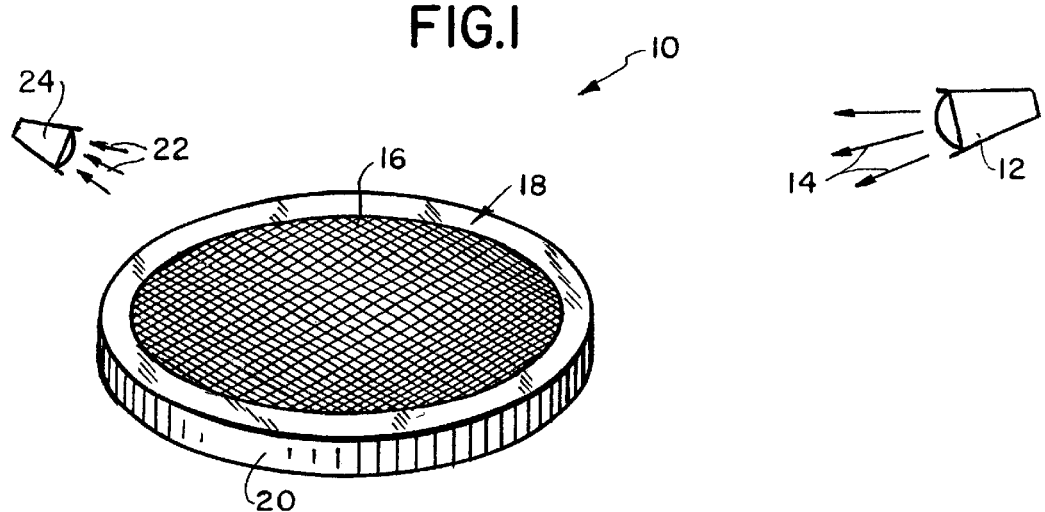
FIG. 1 is a schematic diagram of an inspecting apparatus according to the present invention.

10: Inspecting apparatus
    12, 28, 34: Illuminator for inspection
    14, 31, 33, 38: Light
    16: Finely patterned surface
    18: Substrate
    20: Supporting means.
    22: Diffracted light
    24: Determining means (human eyes)
    26: Resist pattern
    30, 32, 36: Light source
    40: Light conductor

DESCRIPTION OF THE INVENTION

The present invention provides methods and apparatus including, an illuminator, useful for inspection and other applications, which is capable of visually detecting the presence or absence of defocusing and/or other problems on a surface of a semiconductor substrate, such as a wafer, on which resist patterns are finely formed, and widens particularly angle of visual field to improve visual inspection visibility.

The dual peak wavelength tube according to the present invention emits two kinds of lights each having a narrow wavelength range including a peak wavelength at a respective one of two complementary colors. Compared to two colors consisting of the other combination, the two complementary colors have so sharp color contrast that these colors give a glaring and sharp impression to human eyes. Among these two complementary colors are red and blue-green, yellow and blue, and green and brown, or the like, but above all, the combination of red and blue-green is most favorable in view of contrast. The term "complementary colors" includes colors close to the complementary colors and is broadly interpreted in the present invention.

Although the lights applied from the dual peak wavelength tube or dual color tube of the present invention advantageously include only two colors which are complementary to each other, practically, these lights may include light whose wavelength is a little different from the peak wavelengths of the complimentary colors. The dual peak wavelength tube may be a fluorescent tube in which a mixture of a fluorescent material emitting one of the complementary colors and a fluorescent material emitting the other color is deposited inside a glass tube. In the fluorescent material producing one of or the other color of the complementary colors, it may also be possible to obtain suitable colors by adjusting the mixture ratio of two or more kinds of fluorescent materials. In addition, this dual peak wavelength tube may also comprise a discharge tube having two peak wavelengths in the wavelength range of the complementary colors. For example, a hydrogen gas filled discharge tube advantageously has two peak wavelengths of 486 nm, which is analogous to blue-green, and 656 nm, which is analogous to red.

The illuminator for inspection according to the present invention illuminates a surface of a substrate with light at a predetermined angle, on which predetermined patterns are formed to determine the presence or absence of deformations on the finely patterned surface by light diffracted by the finely patterned surface. The illuminator comprises a light source for emitting two kinds of lights each having a narrow wavelength range with a peak wavelength at one of two complementary colors. The above-mentioned dual peak wavelength tube, particularly, a fluorescent tube is advantageously used as a light source of the illuminator.

The inspecting apparatus of the present invention comprises an illuminator for inspection having a light source for emitting lights, supporting means for supporting a substrate having a surface on which predetermined patterns are finely formed, being illuminated at a predetermined angle with the lights by the illuminator, and determining means for determining whether or not the predetermined patterns on the surface of the substrate are deformed using lights diffracted by the finely patterned surface. This illuminator for inspection may apply two kinds of lights each having a narrow wavelength range including a peak wavelength at a respective one of the two complementary colors.

The surface of the substrate on which predetermined patterns are finely formed functions as a diffraction grating, and the lights are reflected and diffracted when the finely patterned surface is irradiated with the lights. When there are no abnormal portions in patterns because of patterns uniformly formed on the substrate, all the lights diffracted by the finely patterned surface are reflected and diffracted in the same direction. Either one of two complementary colors, or a color obtained by combining the two complementary colors, or a state of being dark in which the diffracted lights are invisible, appears on the entire surface depending upon the direction from which these diffracted lights are visually inspected. More particularly, when the substrate (finely patterned surface) is rotated relative to the lights, the colors appear in the order of either one of the two complementary colors, the color obtained by combining the complementary colors, the other color of the complimentary colors, and the color obtained by combining the two complementary colors, and further, the gap between the colors which appear in order turns to look dark according to the conditions, such as the position of the visual inspection.

On the contrary, when there are abnormal portions in the patterns on the substrate caused by defocusing, one of two complementary colors appears on the entire finely patterned surface, while the other color of the complementary colors appears locally in the abnormal portions. Moreover, when the substrate (finely patterned surface) is rotated relative to the lights, on the contrary to the above, the one of the two complementary colors appears locally in the other color. At this time, no colors other than the two colors which are complementary to each other appear even if the substrate is rotated, or the position of human eyes viewing the diffracted lights from the substrate is changed.

For this reason, even though the direction of visual inspection varies, only the complementary colors appear, and a wide angle of view field is obtained. Accordingly, for example, if the two complementary colors are red and blue-green, when blue-green appears in red locally, or when red appears in blue-green locally, it is immediately recognized that the local regions contain abnormalities due to defocusing, or the like. The complementary color pair having thus sharp contrast can dramatically improve the sensitivity of detection of abnormalities, such as defocusing, even though the colors are visually checked.

The finely patterned surface of the substrate, on which two colored lights are applied, functions as a diffracted grating because the two different colored lights which are complementary to each other are used. When nonconforming or abnormal portions caused by defocusing exist on the substrate, normal portions are represented by one of complementary colors, while the abnormal portions are represented by the other of the complimentary colors. Since the colors which are complementary to each other have sharp contrast and appear vividly, they are excellent in visibility in a visual inspection. In addition, due to exclusion of the colors other than the complementary colors, the angle of visual field becomes wider without change of the colors according to the direction of the visual inspection to further improve visibility. Accordingly, even though minor nonconformity such as defocusing is detected, the defective portions can be distinguished by a visual inspection.

Further, if defocusing results from abnormalities of production apparatuses, the visual inspection is also useful to find such abnormalities of apparatuses. Further, defect detection, such as defocusing at an early stage permits reuse of defective products and reduces yielding loss.

DESCRIPTION OF EXAMPLE EMBODIMENTS

Now, example embodiments of the dual peak wavelength tube, illuminator for inspection, inspecting apparatus, and method thereof according to the present invention will be described in detail on the basis of the accompanying drawings.

As shown in FIG. 1, an inspecting apparatus 10 comprises an illuminator 12 for inspection for emitting lights 14, supporting means 20 for supporting a substrate 18 having a surface on which predetermined patterns are finely formed, being illuminated at a predetermined angle with the lights 14 from the illuminator 12, and determining means 24 for determining whether or not the predetermined patterns on the surface of the substrate are deformed due to defocusing by lights 22 diffracted by the finely patterned surface 16. Illuminator 12 is depicted in detail in FIG: 1A and may be a gas filled tube, more specifically, a fluorescent tube comprising any convenient fluorescent material, such as phosphor, 130 which is a thin film coating lining the interior of the light emitting illuminator 12. Further, the tube is filled with a gas medium 131, such as neon in a neon tube. The illuminator 12 for inspection is configured to emit two kinds of lights each having a narrow wavelength range with a peak wavelength at a respective one of the complementary colors. The light from the illuminator should be able to produce interference and diffraction but is not required to be coherent.

Figure 2:
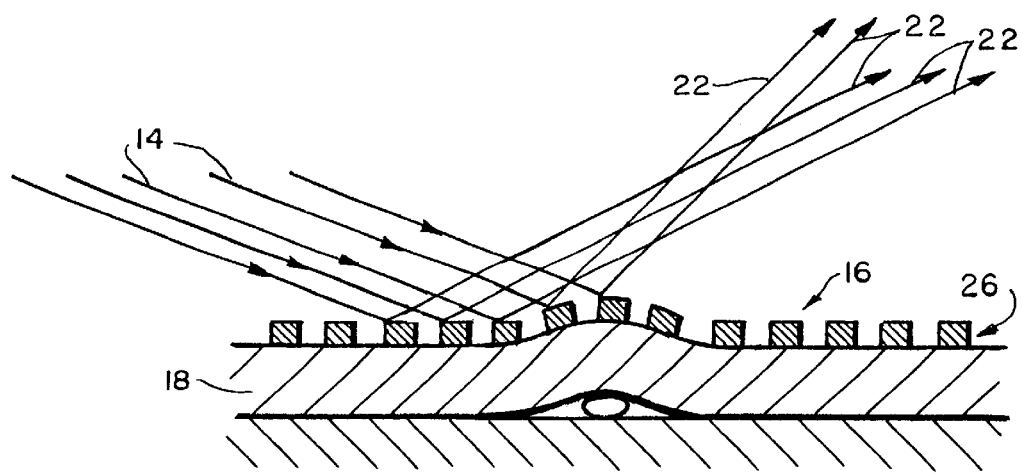
FIG. 2 is a schematic diagram for illustrating the operation of an illuminator for inspection according to the present invention.
Figure 1A:
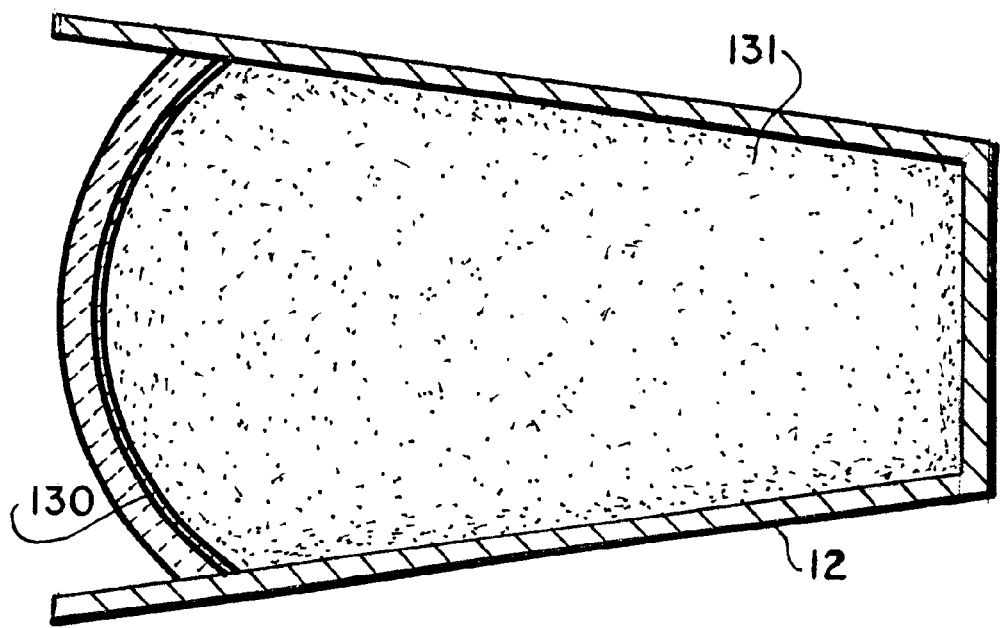
FIG 1A is a detailed view of elements comprising an illuminator of the present invention.

The substrate 18 having the surface 16 on which the predetermined patterns are finely formed herein includes a wafer such as a silicon wafer and a glass substrate, and the like. In addition, the surface 16 where the predetermined patterns finely formed on the substrate 18 includes, as shown in FIG. 2, resist patterns 26 obtained by development after the resist layer is exposed to the predetermined patterns in the lithography method, and a patterned surface obtained by etching a wafer, or a silicon layer, and the like laminated on the glass substrate in accordance with the above resist patterns. The pitch of the resist patterns 26 is advantageously about 3 mm or less, in order to diffract the incoming lights.

The substrate 18 is placed on the supporting means 20, such as a turn table or a fixed table, and is provided in such a manner that the distance between the substrate 18 and the illuminator 12, and the angle between an incident light from the illuminator 12 and the substrate 18 keep constant. When the supporting means is a rotary type, it is generally preferable to identify the presence or absence of deformations on the substrate due to defocusing by rotating the supporting means 20 by 90 degrees to direct the lights from different directions onto the substrate 18 and inspecting the reflected and diffracted lights 22 from the substrate 18.

The illuminator 12 for inspection is an apparatus for applying lights 14 each having a narrow wavelength range which includes a peak wavelength at one of the colors complementary to each other. Advantageously, the illuminator 12 is an apparatus for emitting two different colors complementary to each other from a single light source. In alternate embodiments, there are various combinations of two complementary colors, such as red and blue-green, yellow and blue, and green and brown. In some embodiments, the color combinations include the combination of two colors other than complementary colors which have high color contrast analogous to complementary colors. Although any of the combinations may be employed, above all, the combination of red and blue-green is particularly preferable in view of the contrast effect. The combination of red and blue-green has so strong contrast in color arrangement effect that these colors give a glaring and sharp impression to human eyes. This enables one of the complementary colors to be clearly and visually distinguished from the other.

Advantageously, the lights 14 do not include colors other than the two complementary colors, and each have a narrow wavelength range including a peak wavelength at a respective one of the complimentary colors. As the wavelength region becomes narrower, the more the lights are obtained as monochromatic lights. The lights may practically include wavelengths slightly different from the peak wavelengths of the complimentary colors, however, the light components are best to be ignorably weak compared to the light at a peak wavelength.

The illuminator 12 for inspection is located in such a manner that the incident angle of the light illuminated from the illuminator 12 is advantageously shallow with respect to the substrate 18, for example, 15 degrees or so when the finely patterned pitch is 0.8 mm. In the case of narrower pitch, the incident angle of the light 14 is advantageously narrower than 15 degrees. The distance between the illuminator 12 and the substrate 18 is advantageously, for example, about 500 mm. When the illuminator 12 is too far away from the substrate 18, the contrast of the diffracted lights 22 becomes worse due to deterioration of illumination intensity on the surface of the substrate 18, which leads to an overlook of nonconformity caused by defocusing, and the like. On the contrary, when the illuminator 12 is too close to the substrate 18, deterioration of detection sensitivity is caused by too high illumination intensity on the surface of the substrate 18 because of the narrower range in which the substrate 18 is irradiated by the illuminator 12, as well as becoming a cause of deterioration of eyesight of the operator who visually inspects the diffracted lights 22. According to experiments, the illumination intensity on the surface of the substrate 18 is advantageously 300 Lx or more.

On the other hand, the substrate 18 is located so as to be advantageously about 700 mm away from human eyes which visually inspect the lights 22 diffracted by the substrate 18. When the human eyes are too close to the substrate 18, the eyesight becomes narrower, and when the human eyes are too far away from the substrate 18, the contrast of the diffracted lights becomes worse. Further, in the angle formed by the eyes and the substrate 18, it is preferable to preselect by experiments, or the like the angle at which the human eyes can look at the diffracted lights most easily, but the illuminator 12 for inspection according to the present invention may be roughly set because the angle of view field is wide as will be described later.

The lights 14 applied onto the substrate 18 by the illuminator 12 are reflected and diffracted by the finely patterned surface 16 formed by predetermined patterns on the surface of the substrate 18. When the surface 16 does not contain abnormalities due to defocusing, the diffracted lights 22 are reflected and diffracted in the same direction from the entire surface of the substrate 12, and thus the colors of the diffracted lights 22 visually observed are almost the same. Accordingly, when the substrate 18 is rotated by the supporting means 20, the color observed will change from one of two complementary colors to a mixed color in the direction of 45 degrees, and then to the other color of the complementary colors in the direction of 90 degrees. The gap between colors which appear in succession may look dark depending on the position of the visual inspection. Furthermore, the order of the colors which appear is reversed with the change of the angle at which the visual inspection for the surface of the substrate 18 is conducted.

On the contrary, when there are abnormal portions on the finely patterned surface 16 caused by defocusing, or the like, the lights 22 diffracted by the normal portions give one of the two complementary colors, while the diffracted lights 22 give the other of the complementary colors at the abnormal portions. For example, therefore, if the two complementary colors are red and blue-green, the lights 22 diffracted by the abnormal portions will appear in red when the lights 22 diffracted by the normal portions are in blue-green. When this substrate 18 is allowed to rotate 90 degrees, the lights 22 diffracted from the normal portions appear in red, and the lights 22 diffracted from the abnormal portions appear in blue-green. Even though the substrate 18 is allowed to rotate or the substrate is changed in the direction of the visual inspection, the colors of the diffracted lights 22 are never blurred because the colors other than the two colors which are complementary to each other are not included in the diffracted lights 22. This leads to a wider angle of view field of the diffracted lights 22, and improvement of visual observation visibility, so that nonconformity caused by defocusing can be detected over the entire surface of the substrate 18 by visually inspecting the diffracted lights 22.

Figure 3:
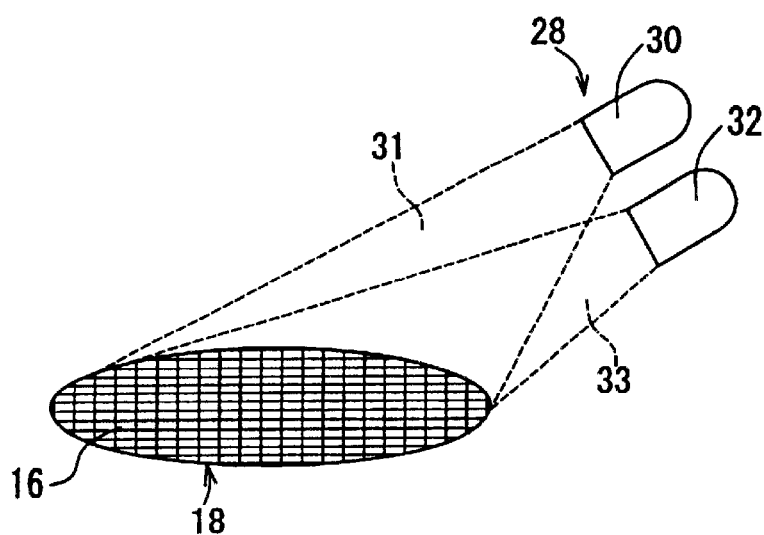
FIG. 3 is a schematic diagram for showing another embodiment of the illuminator for inspection according to the present invention.

Although one embodiment according to the present invention has been described in detail so far, but the present invention is, however, not limited to the above-mentioned embodiment. For example, as shown in FIG. 3, the illuminator 28 for inspection may comprise two light sources 30 and 32 for separately emitting the two complimentary-color lights 31 and 33. The complementary-color lights 31 and 33 are combined into a single beam before the lights reach the substrate 18. Advantageously, the directions of emission of the lights 31 and 33 coincide as much as possible. This illuminator comprises, for example, a light source for emitting red colored lights, and a light source for emitting blue-green colored lights. The division of the light source into two facilitates adjustments so that the brightness of the lights 31 and 33 emitted respectively becomes substantially equal.

When nonconformity caused by defocusing is inspected at the stage of resist patterning, the illuminator is used after its short wavelength range is cut so as to prevent the resist from being exposed to the lights applied by the illuminator. Since inspections for nonconformity caused by defocusing are often performed in the production site, the wavelengths of the illuminator should not be within the short wavelength range corresponding to a photosensitive range of a photosensitive resin, such as a resist.

Figure 4:
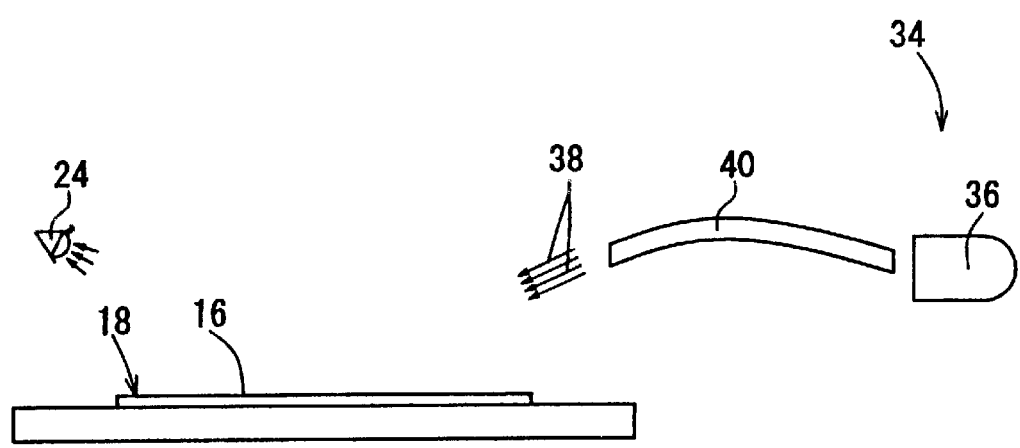
FIG. 4 is a schematic diagram for showing still another embodiment of the illuminator for inspection according to the present invention.

The illuminator for inspection is advantageously arranged in the vicinity of the supporting means on which the substrate is placed, and the surface of the substrate is advantageously illuminated by the illuminator directly. When it is impossible to directly illuminate the surface using the illuminator due to small area for the inspecting apparatus, however, for example, as shown in FIG. 4, the illuminator may include a light conductor 40 which leads the lights 38 emitted by the light source 36 to the surface of the substrate 18 located between the illuminator 34 for inspection and the substrate 18 as well. Although the most preferable light conductor 40 is an optical fiber, it may also be a transparent plate-like substance. With the use of the light conductor 40 having flexibility, such as an optical fiber, setting conditions such as angle of illumination becomes easier.

The light source of the illuminator for inspection according to the present invention comprises a dual peak wavelength or dual color tube for applying the two kinds of lights each having a narrow wavelength range which includes a peak wavelength at a respective one of the two complementary colors. More specifically, two kinds of fluorescent materials which may create the two colors complementary to each other are mixed and uniformly applied inside a glass tube to form a fluorescent tube. Plural kinds of fluorescent materials may be mixed to obtain a color. In addition, the light source may comprise two kinds of fluorescent tubes for creating the complementary color pair.

The dual peak wavelength tube may comprise a discharge tube with two peak wavelengths of two different colors complementary to each other in the wavelength range. For example, a hydrogen gas-filled discharge tube having two peak wavelengths; 486 nm analogous to blue-green and 656 nm analogous to red is particularly preferable. Or such dual peak wavelength tube may comprise a light emitting diode as well, and the light source is not limited to these ones.

When the lights reflected and diffracted by the substrate are visually inspected, it is advantageous that the luminosities of the two colors of the complementary color pair are equal in terms of visibility. The brightness of the two lights is set substantially equal.

The dual peak wavelength tube, illuminator for inspection, inspecting apparatus, and method thereof according to the present invention have been variously described so far, but the present invention is not limited to the embodiments. For example, instead of visual inspection, it is possible to introduce automation by prior art, such as color discrimination using image processing, and distinction of change in the diffracted lights by converting it to electrical signals using a photoelectric converter. In this case, detection accuracy is improved. The present invention is not limited to wafer inspections, but is applicable to other inspections of DVD (Digital Versatile Disk) or CD-ROM (Compact Disk Read Only Memory), or similar inspections and other applications. Also, any modification, variations or equivalent arrangements which may occur to those skilled in the art should be considered to be within the scope of the invention.

There have thus been shown and described a novel dual peak wavelength tube, an illuminator for inspection, an inspection or other application apparatus, and a method thereof which fulfill all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited by the claims which follow.

What is claimed is:

1. An apparatus capable of visually detecting the presence or absence of problems on the surface of a semiconductor substrate on which resist patterns are finely formed comprising:

an illuminator comprising a single dual peak wavelength tube which is a light source emitting two different colors of lights, each said colored light having a narrow wavelength range, with a peak wavelength at a respective one of two complementary colors to each other, said light from said illuminator is capable of producing interference and diffraction but is not required to be coherent;

supporting means for supporting a substrate having a surface on which predetermined patterns are finely formed, said surface being illuminated at a predetermined angle with said lights emanating from said illuminator, said surface functioning as a diffraction grating, and said lights being reflected and diffracted when said predetermined finely patterned surface is irradiated with said light; and determining means for determining whether said predetermined finely pattern surface on said substrate are deformed due to defocusing as a result of said light being diffracted by said finely patterned surface; and wherein when said surface does not contain abnormalities resulting from defocusing, said two diffracted lights are reflected and diffracted in the same direction from the entire surface of said substrate and the colors of the diffracted lights visually observed are substantially the same; and when there are abnormal portions on said finely patterned surface caused by defocusing, said lights diffracted by normal portions give one of the two complementary colors emitted by said source, while the lights diffracted by abnormal portions give the other of the complementary colors.

2. An apparatus according to claim 1, wherein said two kinds of lights are both monochromatic lights.

3. An apparatus according to claim 1, further comprising a fluorescent tube having a plurality of fluorescent materials deposited therein, capable of emitting said two kinds of lights.

4. An apparatus according to claim 1, wherein said single dual peak wavelength tube a gas discharge tube filled with a gas medium capable of emitting said two kinds of lights.

5. An apparatus according to claim 1, wherein the brightness of said two kinds of lights is substantially equal.

6. An apparatus according to claim 1, used for inspection.

* * * * *